(12) United States Patent
Zhang

(10) Patent No.: US 7,163,704 B2
(45) Date of Patent: Jan. 16, 2007

(54) **INJECTION MADE FROM *IXERIS SONCHIFOLIA HANCE* FOR TREATMENT OF CARDIO-CEREBRAL VASCULAR DISEASES AND FUNDUS DISEASES AND METHOD OF PRODUCING THEREOF**

(75) Inventor: Ruixiang Zhang, Liaoning (CN)

(73) Assignee: Maoxiang Wang, Tianjin (CN)

( * ) Notice: Subject to any disclaimer, the term of this patent is extended or adjusted under 35 U.S.C. 154(b) by 14 days.

(21) Appl. No.: 10/511,902

(22) PCT Filed: Apr. 21, 2003

(86) PCT No.: PCT/CN03/00290

§ 371 (c)(1),
(2), (4) Date: Oct. 20, 2004

(87) PCT Pub. No.: WO03/090767

PCT Pub. Date: Nov. 6, 2003

(65) Prior Publication Data

US 2005/0244514 A1    Nov. 3, 2005

(30) Foreign Application Priority Data

Apr. 23, 2002 (CN) ............................... 02 1 09532

(51) Int. Cl.
*A61K 36/00* (2006.01)
(52) U.S. Cl. .................................................... 424/725
(58) Field of Classification Search .................... None
See application file for complete search history.

(56) References Cited

OTHER PUBLICATIONS

English translatin of CN 1346648 A—May 1, 2002.*

* cited by examiner

*Primary Examiner*—Susan Coe
(74) *Attorney, Agent, or Firm*—Fei-Fei Chao; Andrews Kurth LLP

(57) ABSTRACT

The invention discloses an injection made from Chinese herb *Ixeris Sonchifolia Hance* for treatment of cardio-cerebral vascular diseases and fundus diseases and method of producing thereof. The injection is in a form of lyophilized powder in which the rate of flavone to adenosine is 5 mg:15 μg or 5 mg:30 μg. The flavone and adenosine from *Ixeris Sonchifolia Hance* is more stable in the lyophilized powder form than in liquid form for injection so that it is easy to control the quality of the product so as to make the medicament safe and effective. It has benefit in store.

13 Claims, No Drawings

INJECTION MADE FROM *IXERIS SONCHIFOLIA HANCE* FOR TREATMENT OF CARDIO-CEREBRAL VASCULAR DISEASES AND FUNDUS DISEASES AND METHOD OF PRODUCING THEREOF

RELATED APPLICATION

This application claims the priority of PCT Application No. PCT/CN03/00290, filed on Apr. 21, 2003, which claims the priority of China Patent Application No. 02109532.9, filed on Apr. 23, 2002. Both Applications are incorporated herein by reference.

TECHNICAL FIELD

The present invention relates to an injection made from Chinese herb and method of producing thereof, and more particularly to a lyophilized powder of *Ixeris Sonchifolia Hance* for injection and method for producing thereof, for treatment of cardio-cerebral vascular diseases and fundus diseases.

BACKGROUND ART

Currently, Chinese herbal injections for treatment of cardio-cerebral vascular diseases and fundus diseases include *Ixeris Sonchifolia Hance* injection, which for clinical application is a brown-yellow transparent liquid derived from *Ixeris Sonchifolia Hance* of *Compositae* and extracted as intravenous injection starting from full plants. The main pharmaceutical components of the intravenous injection are flavone and adenosine. The coexistence of phyto-flavone and -adenosine in *Ixeris Sonchifolia Hance* has shown a remarkable complementary effect for treatment of cardio-cerebral diseases, which has already been demonstrated by pharmacodynamics study and clinical application. The pharmacological effects of *Ixeris Sonchifolia Hance* injection consist in its efficacies of: 1. increasing coronary artery flow, lowering cardiovascular resistance, resisting myocardial infarction, enhancing collateral circulations, reducing myocardial oxygen consumption and improving cardio-microcirculations, which are useful for the treatment of coronary heart diseases, angina pectoris, chest distress and breath shortness, and myocardial infarction; 2. reducing platelet conglomeration, increasing the activity of fibrinolysin, inhibiting thrombosis, decreasing the viscosity of blood plasma and serum, increasing the electrophoresis velocity of erythrocytes, lowering cerebro-vascular resistance, increasing cerebral blood capacity and promoting restoration of neural function, which are useful in the treatment of cerebral infarction (cerebral thrombosis); 3. improving microcirculation disorders caused by bacteria, systemic microcirculation disorders caused by polymer dextran, and fundus microcirculation, and dilating fundus artery, which are useful in the treatment of fundus diseases, such as central retinitis, optic atrophy and retinitis pigmentosa. However, *Ixeris Sonchifolia Hance* injections exhibit poor stability and can only stand short-term storage. The contents of flavone and adenosine have been determined by High Performance Liquid chromatography (HPLC) and derivatization method, which show that adenosine content reduces from 15.0 µg/ml prior to finishing of the aqueous injection to 6.7 µg/ml thereafter, while for flavone, from 0.25 mg/ml to 0.169 mg/ml, with a lose of 55.3% and 32.4% of the prescribed, respectively. Six months later, adenosine content reduces to 6.5 µg/ml, while flavone content is 0.133 mg/ml. This can also be verified by subjecting *Ixeris Sonchifolia Hance* aqueous injection wherein flavone and adenosine contents are respectively 5.07 mg/ml and 24.37 µg/ml, to ten-day accelerated stress test carried out at 80° C. in an oven, followed by content determination of both, in doing so, merely 3.16 mg/ml and 12.18 µg/ml are left for flavone and adenosine, respectively (Tab. 1). In view of the considerable lose of both active ingredients of flavone and adenosine during preparation and storage, the therapeutic effect of the injection is seriously impacted. Moreover, *Ixeris Sonchifolia Hance* injection exhibits a distinct change in color of solution. The absorbance measured at 400 nm using ultraviolet spectrophotometer during preparation of the aqueous injection from stock extract, ranges from 0.338 prior to sterilization to 0.423 thereafter, and further increases to 0.443 after 6 months with darkened color. It should be further noted that HPLC spectra of the injection exhibit poor similarity, that is to say, there exist major differences among HPLC spectra of different batches of aqueous injections yet formulated from the same stock extract. The stability behavior of same kind of commercial aqueous injections by random sampling (Batch No. 20000303, 20000503, 20010120) shows that: flavone contents are 0.27 mg/ml, 0.51 mg/ml and 0.30 mg/ml, while for adenosine, the contents are 1.11 µg/ml, 0.147 µg/ml and 0.00 µg/ml, respectively In a conclusion, *Ixeris Sonchifolia Hance* aqueous injection is susceptible to various factors such as preparation, storage, and thus is difficult to be controlled in quality, which greatly expenses the therapeutic effect of *Ixeris Sonchifolia Hance* injection.

CONTENTS OF THE INVENTION

The object of the present invention is to provide a Chinese herbal injection for treatment of cardio-cerebral vascular diseases and fundus diseases, and method of producing thereof, which not only overcome the defects existing with *Ixeris Sonchifolia Hance* aqueous injection, but allow stable and readily controlled quality, little lose of flavone and adenosine contents, therefore ensure a more safe and effective clinical use, and be of great advantage for storage.

The object of the invention is achieved by a Chinese herbal injection for treatment of cardio-cerebral vascular diseases and fundus diseases, characterized in that it is in a form of lyophilized powder of *Ixeris Sonchifolia Hance* for injection, wherein the content ratio of flavone to adenosine is 5 mg 15 µg or 5 mg:30 µg.

The method of producing the Chinese herbal injection according to the invention is effected as following: clean *Ixeris Sonchifolia Hance* is added to 25~30 times amount of water for 3 hours decoction, strained, micro-strained and concentrated until 1 ml of concentrate corresponds to 0.5 g of crude herb; the concentrated decocting solution is then cooled to below 40° C., and 10% calcium oxide emulsion is added under stirring to adjust pH to 10~11, filtered, and the precipitate is weighed; said precipitate is suspended in 5.3 times of ethanol, 25% strength of sulfuric acid solution is added to adjust pH to 3~4, followed by through stirring and filtration; 40% sodium hydroxide solution is added to the filtrate and adjusted pH to 7~7.5, filtered, and ethanol is then recovered therefrom and eliminated by evaporation, water for injection is added to allow 1 ml as corresponding to 4 g of crude herb; then refrigerated below −8° C. for 12 hours, filtrated; boiled for 15 minutes by adding 0.1~0.2% active carbon, and allowed to stand at −5° C. for more than 24 hours, filtrated, adjusted to pH 7.0~7.5, then filtered through cardboard, sintered funnel and microporous membrane (pore diameter of 0.45 µm), sealed after filling, and sterilized (115° C., 30 min), to provide the extract; to said extract is added stabilizing agents or subsequently supporting agents, and stirred to allow complete dissolution, further treated by adding active carbon for injection, and filtrated, the resulting transparent non-pyrogen solution is then charged in vials or ampoules, pre-frozen at −40~−60° C. for 1~3 hours, vacuumed (vacuum degree of 1~20 Pa) by suction, and dried at elevating temperature for 20~40 hours to the final of 25~40° C. Lyophilized powder of *Ixeris Sonchifolia Hance* for injection is thus obtained.

The benefits of the invention consist in that: by formulating *Ixeris Sonchifolia Hance* containing flavone and adenosine into lyophilized powder of *Ixeris Sonchifolia Hance* for injection, the defects of unstable quality and loss of flavone and adenosine going with said *Ixeris Sonchifolia Hance* aqueous injection are overcome, in addition, easy control of quality, little lose of flavone and adenosine contents have been achieved, therefore ensuring a more safe and effective clinical use, and be of great advantage for storage.

SPECIFIC EMBODIMENTS

EXAMPLE 1

1 kg of clean *Ixeris Sonchifolia Hance* are put into a decocting pot, to which 25~30 times amount of water are poured over for 3 hours decoction. The decocting mixture is strained, microstrained, and then transferred to a concentrator for concentration until 1 ml of the concentrate corresponds to 0.5 g of crude herb. The concentrated solution is then allowed to cool to 39° C., stirred and added with 10% calcium oxide emulsion to adjust pH to 10. After filtration, the precipitate formed is taken for weighing, then suspended in an amount of ethanol 5.3 times by weight of the precipitate itself, and 25% strength of sulfuric acid solution is further added thereto to adjust pH to 3. The suspension is well stirred, filtered, and 40% sodium hydroxide solution is then added to the filtrate to bring pH to 7. After filtration, ethanol is recovered from the filtrate and subsequently eliminated by evaporation. Water for injection is then added until 1 ml corresponds to 4 g of crude herb, which is then refrigerated at −9° C. for 12 hours, filtered, boiled for 15 minutes by adding 0.1% active carbon, and further allowed to stand at −5° C. for 24 hours. The solution is further filtered, adjusted to pH 7, then filtered through cardboard, sintered funnel and microporous membrane (pore diameter of 0.45 μm), sealed after filling, and sterilized (115° C., 30 min), to provide the extract. To the extract obtained is added 0.05% EDTA or sodium citrate as stabilizing agent, and stirred to allow complete dissolution, further treated by adding 0.1% active carbon for injection, and filtered. The resulting transparent non-pyrogen solution is then charged in each vial or ampoule of 2 ml, pre-frozen at −40° C. for 3 hours, vacuumed by suction (vacuum degree of 15 Pa), and dried at elevating temperature for 20 hours to the final of 25° C. Lyophilized powder of *Ixeris Sonchifolia Hance* for injection thus is prepared.

EXAMPLE 2

1 kg of clean *Ixeris Sonchifolia Hance* are put into a decocting pot, to which 25~30 times amount of water are poured over for 3 hours decoction. The decocting mixture is strained, microstrained, and then transferred to a concentrator for concentration until 1 ml of the concentrate corresponds to 0.5 g of crude herb. The concentrated solution is then allowed to cool to 35° C., stirred and added with 10% calcium oxide emulsion to adjust pH to 10. After filtration, the precipitate formed is taken for weighing, then suspended in an amount of ethanol 5.3 times by weight of the precipitate itself, and 25% strength of sulfuric acid solution is further added thereto to adjust pH to 3.5. The suspension is well stirred, filtered, and 40% sodium hydroxide solution is then added to the filtrate to bring pH to 7.3. After filtration, ethanol is recovered from the filtrate and subsequently eliminated by evaporation. Water for injection is then added until 1 ml corresponds to 4 g of crude herb, which is then refrigerated at −10° C. for 12 hours, filtered, boiled for 15 minutes by adding 0.12% active carbon, and further allowed to stand at −5° C. for 25 hours. The solution is further filtered, adjusted to pH 7.2, then filtered through cardboard, sintered funnel and microporous membrane (pore diameter of 0.45 μm), sealed after filling, and sterilized (115° C., 30 min), to provide the extract. To the extract obtained are added 0.1% sodium bisulfite or sodium pyrosulfite or mixture thereof as stabilizing agent and 3% mannitol as supporting agent, stirred to allow complete dissolution, further treated by adding 0.05% active carbon for injection, and filtered. The resulting transparent non-pyrogen solution is then charged in each vial or ampoule of 3 ml, pre-frozen at −45° C. for 2.5 hours, vacuumed by suction (vacuum degree of 18 Pa), and dried at elevating temperature for 30 hours to the final of 30° C. Lyophilized powder of *Ixeris Sonchifolia Hance* for injection thus is prepared.

EXAMPLE 3

1 kg of clean *Ixeris Sonchifolia Hance* are put into a decocting pot, to which 25~30 times amount of water are poured over for 3 hours decoction. The decocting mixture is strained, microstrained, and then transferred to a concentrator for concentration until 1 ml of the concentrate corresponds to 0.5 g of crude herb. The concentrated solution is then allowed to cool to 20° C., stirred and added with 10% calcium oxide emulsion to adjust pH to 10.5. After settling for 12 hours, the precipitate is filtered off and weighed, then suspended in an amount of ethanol 5.3 times by weight of the precipitate itself, and 25% strength of sulfuric acid solution is further added thereto to adjust pH to 4. The suspension is well stirred, filtered, and 40% sodium hydroxide solution is then added to the filtrate to bring pH to 7. After filtration, ethanol is recovered from the filtrate and subsequently eliminated by evaporation. Water for injection is then added until 1 ml corresponds to 4 g of crude herb, which is then refrigerated at −11° C. for 12 hours, filtered, boiled for 15 minutes by adding 0.15% active carbon, and further allowed to stand at −5° C. for 24 hours. The solution is further filtered, adjusted to pH 7.4, then filtered through cardboard, sintered funnel and microporous membrane (pore diameter of 0.45 μm), sealed after filling, and sterilized (115° C., 30 min), to provide the extract. To the extract obtained are added 0.05% sodium sulfite or ascorbic acid or mixture thereof as stabilizing agent, or gassed with nitrogen, and then 3% dextran as supporting agent, stirred to allow complete dissolution, further treated by adding 0.05% active carbon for injection, and filtered. The resulting transparent non-pyrogen solution is then charged in each vial or ampoule of 1 ml, pre-frozen at −50° C. for 2 hours, vacuumed by suction (vacuum degree of 10 Pa), and dried at elevating temperature for 25 hours to the final of 35° C. Lyophilized powder of *Ixeris Sonchifolia Hance* for injection thus is prepared.

EXAMPLE 4

1 kg of clean *Ixeris Sonchifolia Hance* are put into a decocting pot, to which 25~30 times amount of water are poured over for 3 hours decoction. The decocting mixture is strained, microstrained, and then transferred to a concentrator for concentration until 1 ml of the concentrate corresponds to 0.5 g of crude herb. The concentrated solution is then allowed to cool to 10° C., stirred and added with 10% calcium oxide emulsion to adjust pH to 11. After filtration, the precipitate is taken for weighing, then suspended in an amount of ethanol 5.3 times by weight of the precipitate itself, and 25% strength of sulfuric acid solution is further added thereto to adjust pH to 3. The suspension is well stirred, filtered, and 40% sodium hydroxide solution is then added to the filtrate to bring pH to 7. After filtration, ethanol is recovered from the filtrate and subsequently eliminated by evaporation. Water for injection is then added until 1 ml corresponds to 4 g of crude herb, which is then refrigerated at −12° C. for 12 hours, filtered, boiled for 15 minutes by adding 0.2% active carbon, and further allowed to stand at −5° C. for 24 hours. The solution is further filtered, adjusted to pH 7.5, then filtered through cardboard, sintered funnel and microporous membrane (pore diameter of 0.45 μm), sealed after filling, and sterilized (115° C., 30 min), to provide the extract. To the extract obtained are added 0.02% sodium thiosulfate as stabilizing agent, and 5% lactose or glucose or mixture thereof as supporting agent, stirred to allow complete dissolution, further treated by adding 0.01% active carbon for injection, and filtered. The resulting transparent non-pyrogen solution is then charged in each vial or ampoule of 4 ml or 5 ml, pre-frozen at −60° C. for 1 hour, vacuumed by suction (vacuum degree of 20 Pa), and dried at elevating temperature for 40 hours to the final of 40° C. Lyophilized powder of *Ixeris Sonchifolia Hance* for injection thus is prepared.

The stabilities under high temperature of flavone content and adenosine content in the lyophilized powder for injection and aqueous injection are compared in Tab. 1.

| No. | Dosage from | Flavone (mg/ml) (pre-test) | Flavone (mg/ml) (post-test) | Adenosine (μg/ml) (pre-test) | Adenosine (μg/ml) (post-test) | Appearance |
|---|---|---|---|---|---|---|
| 1 | Lyophililized powder for injection | 5.07 | 5.03 | 24.37 | 23.88 | Yellow-brown after dissolving in water |
| 2 | Aqueous injection | 5.07 | 3.16 | 24.37 | 12.18 | Dark brown-yellow |

Lyophilized powder of *Ixeris Sonchifolia Hance* for injection is formulated as an injection solution containing 5.07 mg/ml flavone and 24.37 μg/ml adenosine, which is subjected to 10-day accelerated stress test at 80° C. in an oven, then both contents are determined. The contents of flavone and adenosine almost remain unchanged as 5.03 mg/ml and 23.88 μg/ml, while for the aqueous injection, said contents have reduced to 62.33% and 49.99% of the original values.

During clinical application, depending on the requirement of individual condition, different specifications of Lyophilized powder of *Ixeris Sonchifolia Hance* for injection can be dissolved in water for injection, and further added to 250 ml sodium chloride or glucose injection for intravenous infusion.

The invention claimed is:

1. An herbal extract for injection comprising a lyophilized powder of *Ixeris Sonchifolia Hance* having a ratio of flavone to adenosine of about 5 mg:15 g or 15 mg:30 g; wherein said herbal extract treats patients with cardio-cerebral diseases and fundus diseases.

2. A method for producing the herbal extract for injection according to claim 1, comprising:
   decocting *Ixeris Sonchifolia Hance* in water to form a decocting mixture;
   concentrating said decocting mixture to form a concentrate;
   adding a calcium oxide emulsion to said concentrate to adjust a pH to about 10–11;
   filtering and precipitating said pH adjusted concentrate to obtain a precipitant;
   suspending said precipitant in ethanol to form a suspension;
   adjusting said suspension to a pH to about 3–4 by an acidic solution to form an acidic suspension;
   filtering said acidic suspension to obtain a filtrate;
   adding a NaOH solution to said filtrate to adjust a pH to about 7–7.5 to obtain an NaOH-treated filtrate;
   evaporating said ethanol from said NaOH-treated filtrate;
   adding water for injection to said ethanol-evaporated NaOH-treated filtrate to form a solution for injection;
   adding an active carbon to said solution for injection to form a mixture;
   boiling said mixture and then allowing said mixture to cool down;
   filtering out said active carbon from said mixture to collect said herbal extract;
   lyophilizing said herbal extract to form said lyophilized powder of *Ixeris Sonchifolia Hance*.

3. The method as claimed in claim 2, further comprising adding a stabilizing agent to said herbal extract; wherein said stabilizing agent is at least one selected from the group consisting of EDTA, citric acid, sodium citrate, sodium bisulfite, sodium sulfite, sodium pyrosulfite, sodium thiosulfate, ascorbic acid and nitrogen.

4. The method as claimed in claim 2, further comprising adding an excipient agent to said herbal extract; wherein said excipient agent is at least one selected from the group consisting of mannitol, dextran, lactose and glucose.

5. The method according to claim 2, wherein said decocting mixture contains *Ixeris Sonchifolia Hance* and water in a ratio of about 1 kg:25–30 L.

6. The method according to claim 2, wherein said concentrate is in a ratio of about 0.5 kg:1 ml of *Ixeris Sonchifolia Hance* to water.

7. The method according to claim 2, wherein said calcium oxide emulsion is a 10% calcium oxide emulsion.

8. The method according to claim 2, wherein said acidic solution is a sulfuric acid solution.

9. The method according to claim 8, wherein said sulfuric acid is a 25% sulfuric acid.

10. The method according to claim 2, wherein said NaOH solution is a 40% NaOH solution.

11. The method according to claim 2, wherein said active carbon is about 0.1 to 0.2% (w/v) of said solution for injection.

12. The method according to claim 2, wherein said herbal extract is sterilized.

13. The method according to claim 12, wherein said sterilized herbal extract is vacuumed by suction and dried at 25–40° C. to form said lyophilized powder of *Ixeris Sonchifolia Hance*.

* * * * *